United States Patent [19]

Cotton et al.

[11] Patent Number: 5,081,107
[45] Date of Patent: Jan. 14, 1992

[54] POLYPEPTIDE COMPOUNDS

[75] Inventors: Ronald Cotton, Congleton; Anand S. Dutta, Hazel Grove, both of United Kingdom

[73] Assignee: Imperial Chemical Industries PLC, London, England

[21] Appl. No.: 362,337

[22] Filed: Jun. 6, 1989

[30] Foreign Application Priority Data

Jun. 6, 1988 [GB] United Kingdom ............... 8813356

[51] Int. Cl.$^5$ .................... A61K 37/02; C07K 7/06
[52] U.S. Cl. ........................... 514/16; 514/17; 514/15; 530/329; 530/328; 530/327; 530/326
[58] Field of Search .............. 530/326, 327, 328, 329; 514/15, 16, 17

[56] References Cited

U.S. PATENT DOCUMENTS

| | | | |
|---|---|---|---|
| 4,405,778 | 9/1983 | Scartazzini et al. | 514/16 |
| 4,943,561 | 7/1990 | Heimbrook et al. | 514/17 |

FOREIGN PATENT DOCUMENTS

| | | |
|---|---|---|
| 211267 | 2/1987 | European Pat. Off. |
| 309297 | 3/1989 | European Pat. Off. |
| 315367 | 4/1990 | European Pat. Off. |
| 402852 | 12/1990 | European Pat. Off. |
| 8302272 | 7/1983 | World Int. Prop. O. |
| 8809780 | 8/1985 | World Int. Prop. O. |

OTHER PUBLICATIONS

Heimbrook et al., Minimal Ligand Analysis of Gastrin Releasing Peptide,, 1988, pp. 7016–7019.
Coy et al., Probing Peptide Backbone Function in Bombesin, 1988, pp. 5056–5060.

*Primary Examiner*—Lester L. Lee
*Assistant Examiner*—Avis Davenport
*Attorney, Agent, or Firm*—Cushman, Darby & Cushman

[57] ABSTRACT

The invention releates to a polypeptide of formula I

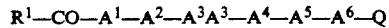

wherein each of the generic terms is disclosed in full in the specification and includes $R^1$ is a 5- or 6-membered unsaturated heterocyclic ring which contains one, two or three nitrogen atoms, which ring may optionally bear one or two substituents; $a^1$ is a direct link to $A^2$; or is His or D-His; $A^2$ is Trp or MeTrp; $A^3$ is Ala or MeAla; $A^4$ is Val; $A^5$ is Gly or D-Ala; $A^6$ is His or Lys(Z); and Q is a group of the formula —$A^7.R^2$ in which $A^7$ is Leu or LeMeu and $R^2$ is hydroxy, amino, (1-3C)alkylamino or (1-3C)alkoxy; or Q is (1-6C)alkoxy or (1-10C)alkylamino.

The compounds possess antagonist properties against bombesin-like peptides and are of value in the treatment of malignant disease in warm-blooded animals.

9 Claims, No Drawings

POLYPEPTIDE COMPOUNDS

This invention relates to polypeptide compounds which possess antagonist properties against bombesin or bombesin-like peptides, hereinafter referred to as bombesin antagonist properties, and are of, value for example in the treatment of malignant disease in warm-blooded animals such as man. The invention includes novel polypeptide compounds and processes for their manufacture; novel pharmaceutical compositions containing said polypeptide compounds and processes for the manufacture of medicaments containing them for use in producing a bombesin antagonist effect in warm-blooded animals such as man.

Bombesin is a tetradecapeptide amide which was first isolated from the skin of the frog Bombina bombina (Anastasi, Erspamer and Bucci, *Experientia*, 1971, 27, 166). It is known that bombesin is a potent mitogen for mouse Swiss 3T3 fibroblast cells (Rozengurt and Sinnett-Smith, *Proc. Natl. Acad. Sci. USA*, 1983, 80, 2936) and that it stimulates amylase secretion from guinea pig pancreatic acini (Jensen, Jones, Folkers and Gardner, *Nature*, 1984, 309, 61). It is also known that bombesin-like peptides are produced and secreted by human small-cell lung cancer (SCLC) cells (Moody, Pert, Gazdar, Carney and Minna, *Science*, 1981, 214, 1246), that exogenously added bombesin-like peptides can stimulate the growth of human SCLC cells in vitro (Carney, Cuttita, Moody and Minna, *Cancer Research*, 1987, 47, 821) and that a monoclonal antibody specific for the C-terminus region of bombesin can prevent the growth of human SCLC cells both in vitro and in vivo (Cuttita, Carney, Mulshine, Moody, Fedorko, Fischler and Minna, *Nature*, 1985, 316, 823).

Gastrin releasing peptide (GRP) is a 27 amino acid peptide amide isolated from the porcine gut (McDonald, Jornvall, Nilsson, Vagne, Ghatei, Bloom and Mutt, *Biochem. Biophys. Res. Commun.*, 1979, 90, 227) in which the C-terminus amino acid sequence is almost identical to that of bombesin. Neuromedin C (or GRP (18–27)) is a decapeptide amide, the structure of which is identical to the last ten amino acids in the C-terminus region of GRP, which has been isolated from the canine small intestine (Reeve, Walsh, Chew, Clark, Hawke and Shively, *J. Biol. Chem.*, 1983, 258, 5582). Both GRP and Neuromedin C possess bombesin-like properties (Zachary and Rozengurt, *Proc. Natl. Acad. Sci. USA*, 1985, 82, 7616). The structures of bombesin and Neuromedin C are shown below:

Bombesin Glp—Gln—Arg—Leu—Gly—Asn—Gln—Trp—Ala—Val—Gly—His—Leu—Met—NH$_2$

Neuromedin C H—Gly—Asn—His—Trp—Ala—Val—Gly—His—Leu—Met—NH$_2$

Several bombesin antagonists are known whereby the structure of the undecapeptide, substance P, is modified by the replacement of several of its L amino acids with D amino acids (Jensen, Jones, Folkers and Gardner, *Nature*, 1984, 309, 61; Zachary and Rozengurt, *Proc. Natl. Acad. Sci. USA*, 1985, 82, 7616 and Heinz-Erian, Folkers, Gardner and Jensen, *Gastroenterology*, 1986, 90, 1455). A few bombesin antagonists derived from the structure of bombesin have also been disclosed: thus [D—Glp$^7$, D—Ala$^{11}$, Ala$^{14}$]bombesin (7–14) was stated to be a partial antagonist of bombesin-induced hypothermia in the rat (Markl, Brown and Rivier, *Peptides*, 1981, 2, Suppl. 2, 169) and [D-Phe$^{12}$]bombesin, [D—Phe$^{12}$, Leu$^{14}$]bombesin and [Tyr$^4$, D—Phe$^{12}$]bombesin inhibited bombesin-stimulated secretion of amylase from guinea pig pancreatic acini (Heinz-Erian, Coy, Tamura, Jones, Gardner and Jensen, *Amer. J. Physiol.*, 1987, 252, G439).

In addition it has been disclosed that [Leu$^{13}$-$\psi$ (CH$_2$—NH)—Leu$^{14}$]bombesin and [Ala$^9$-$\psi$ (CH$_2$—NH) Val$^{10}$, Leu$^{14}$]bombesin are bombesin antagonists (Coy, Heinz-Erian, Jiang and Jensen, *Regulatory Peptides*, 1987, 19, 105; International Symposium on Bombesin-like Peptides, Rome, October, 1987; Coy et al., *J. Biol. Chem.*, 1988, 263, 5056).

It has now been discovered that certain Neuromedin C derivatives are potent bombesin antagonists and this is a basis for the invention.

According to the invention there is provided a polypeptide of formula I:

R$^1$—CO—A$^1$—A$^2$—A$^3$—A$^4$—A$^5$—A$^6$—Q    I wherein R$^1$ is a 5- or 6-membered unsaturated heterocyclic ring which contains one, two or three nitrogen atoms, which heterocyclic ring may be a single ring or may be fused to a benzo-ring, and which heterocyclic ring may optionally bear one or two substituents selected from halogeno, (1–4C)alkyl, (1–4C)alkoxy, hydroxy, cyano and nitro; wherein A$^1$ is a direct link to A$^2$, or is His, D—His, MeHis, EtHis, PrHis, D—Gln, D—Glu(OMe), Leu, MeLeu, D—Leu, Lys(CO-4 Pyridyl), Pal, D—Pal, Phe, D—Phe, Pro, Arg, Glu, His($\tau$-Me), His($\pi$-Me), His(COPh) or Trp;

wherein A$^2$ is Trp, MeTrp, Trp(Me), Trp(For), Val, DL—Flg, L—Nal, pcF, Leu, Lys, Pal or Cha;

wherein A$^3$ is Ala, MeAla, Aib, Gly, Pro, Leu, Phe, Ser, Val, L—Nal, Thr or Glu;

wherein A$^4$ is Val, Aib, Leu, Ile, Thr, Phe, Ser or DL—Flg;

wherein A$^5$ is Gly, Sar, D—Ala, D—Ser, D—Ser(CH$_2$Ph), D—pcF, D—Ala(NH$_2$), D—Ala(NHZ(Cl)), Aib, D—Pro, D—Lys, D—Arg, Ac$^3$c, Ac$^5$c or Ac$^6$c;

wherein A$^6$ is His, MeHis, His($\pi$-Me), His($p$-Me), Aib, Val, Leu, Ala, Ile, Ahx, Ape, Met, Pro, Phe, Gln, Lys, Lys(Z), Lys(COCH$_3$), Lys(COPh), Lys(COCH$_2$Ph), Lys(COCH$_2$CH$_2$Ph), Pal, Ser, Ser(CH$_2$Ph), Thr, Thr(CH$_2$Ph), Glu, Asp, Asp(OBu$^t$), Trp or L—Nal; and wherein Q is a group of the formula —A$^7$·R$^2$ in which A$^7$ is Leu, D—Leu, MeLeu, Ile, MeIle, Ahx, MeAhx, Aib, Pro, Val, MeVal, Phe, Ape, MeApe, Met, Ser, Gln or Trp and R$^2$ is hydroxy or amino; or R$^2$ is (1–3C)alkylamino, dialkylamino of up to 4 carbon atoms, or (1–3C)alkoxy, each optionally bearing a hydroxy, (1–3C)alkoxy, amino, (1–6)alkylamino, dialkylamino of up to 8 carbon atoms, or phenyl (1–3C)alkylamino substituent, other than in a position alpha to an oxygen or nitrogen atom, or a fluoro-(1–3C)alkyl or phenyl substituent; or R$^2$ is (3–6C)cycloalkylamino, N-alkyl-N-cycloalkylamino of up to 8 carbon atoms, or dicycloalkylamino of up to 12 carbon atoms; or R$^2$ is 1-pyrrolidinyl, piperidino, morpholino, 1-piperazinyl or 4-methylpiperazin-1-yl; or Q is (1-6C)alkoxy, (1-10C)alkylamino or dialkylamino of up to 10 carbon atoms each optionally bearing a hydroxy, amino, (1-3C)alkoxy, (1-6C)alkylamino, dialkylamino of up to 8 carbon atoms, phenyl-(1-3C)alkylamino substituent, other than in a position alpha to an oxygen or nitrogen atom, or a phenyl substituent; or Q is phenyl (1-3C)alkylamino; or Q is (3-6C)cycloalkylamino, N-alkyl-N-cycloalkylamino of up to 8 carbon atoms or dicycloalkylamino of up to 12 carbon atoms; or Q is 1-azetidinyl, 1-pyrrolidinyl, piperidino, morpholino, 1-piperazinyl or 1-homopiperidinyl each optionally bearing on any available position, including on any available nitrogen atom, a substituent selected from (1-6C)alkyl, phenyl and phenyl-(1-3C)alkyl; and wherein within $R^2$ or Q a phenyl group may optionally bear a substituent selected from halogeno, (1-4C)alkyl, (1-4C)alkoxy, hydroxy and cyano;

or a pharmaceutically-acceptable salt of said polypeptide.

In this specification the term "alkyl" includes both straight and branched alkyl groups but references to individual alkyl groups such as "propyl" are specific for the straight chain version only. An analogous convention applies to other generic terms.

In the above formula I and throughout this specification, the amino acid residues are designated by their standard abbreviations (Pure and Applied Chemistry, 1974, 40, 317 331; European Journal of Biochemistry, 1984, 138, 9-37).

For the avoidance of doubt it is stated that: amino acid symbols denote the L configuration unless otherwise indicated by D or DL appearing before the symbol and separated from it by a hyphen;

Nal designates 3-(2-naphthyl)alanine, i.e. 2-amino-3-(2-naphthyl)propanoic acid;

pcF designates 4-chlorophenylalanine, i.e. 2-amino-3-(4-chlorophenyl)propanoic acid;

Pal designates 3-(3-pyridyl)alanine i.e. 2-amino-3-(3-pyridyl)propanoic acid;

Flg designates 2-(9-fluorenyl)glycine i.e. 2-amino-2-(9-fluorenyl)acetic acid;

Cha designates 3-cyclohexylalanine i.e. 2-amino-3-cyclohexylpropanoic acid;

Aib designates 2-aminoisobutyric acid i.e. 2-amino-2-methylpropanoic acid;

Sar designates sarcosine i.e. N methylglycine;

Ala(NH$_2$) designates 3-aminoalanine, i.e. 2,3-diaminopropanoic acid;

Ala(NHZ(Cl)) designates 3-(4-chlorobenzyloxycarbonylamino)alanine i.e.
2-amino-3-(4-chlorobenzyloxycarbonylamino)propanoic acid;

$Ac^3c$ designates 1-amino-1-cyclopropanecarboxylic acid;

$Ac^5c$ designates 1-amino-1-cyclopentanecarboxylic acid;

$Ac^6c$ designates 1-amino-1-cyclohexanecarboxylic acid;

Ahx designates (2S)-2-aminohexanoic acid, i.e. norleucine;

Ape designates (2S)-2-aminopentanoic acid, i.e. norvaline;

Lys(CO 4-Pyridyl) designates $N^6$-isonicotinoyllysine i.e. 2-amino-6-isonicotinoylhexanoic acid;

Lys(Z) designates $N^6$-(benzyloxycarbonyl)lysine;

Lys(COCH$_3$) designates $N^6$-acetyllysine;

Lys(COPh) designates $N^6$-benzoyllysine;

Lys(COCH$_2$Ph) designates $N^6$-(phenylacetyl)lysine;

Lys(COCH$_2$CH$_2$Ph) designates $N^6$-(3-phenylpropionyl)lysine;

Thr(CH$_2$Ph) designates $O^3$-benzylthreonine i.e. 2-amino-3-benzyloxybutanoic acid; and Ser(CH$_2$Ph) designates $O^3$-benzylserine i.e. 2-amino-3-benzyloxypropanoic acid.

Suitable values for the generic radicals referred to above include those set out below.

A suitable value for $R^1$ when it is a 5- or 6-membered unsaturated heterocyclic ring which contains one, two or three nitrogen atoms is, for example, pyrrolyl, indolyl, pyridyl, quinolyl, isoquinolyl, imidazolyl, pyrazolyl, benzimidazolyl, indazolyl, pyrimidinyl, pyridazinyl, pyrazinyl, 1,2,3-triazolyl or 1,2,4-triazolyl, which may be attached through any available position including through any available nitrogen atoms and which may bear one or two substituents including a substituent on any available nitrogen atom.

Suitable values for substituents which may be present on a 5- or 6-membered unsaturated heterocyclic ring include the following, for example:

for halogeno: fluoro, chloro, bromo and iodo; for (1-4C)alkyl: methyl, ethyl, propyl, isopropyl and butyl; for (1-4C)alkoxy: methoxy, ethoxy, propoxy, isopropoxy and butoxy.

A suitable value for $R^2$ when it is (1-3C)alkylamino or dialkylamino of up to 4-carbon atoms is, for example, methylamino, dimethylamino, ethylamino, N-ethyl-N-methylamino, propylamino, isopropylamino or diethylamino.

A suitable value for $R^2$, a substituent on $R^2$, or a substituent on Q when it is (1-3C)alkoxy is, for example, methoxy, ethoxy, propoxy or isopropoxy.

A suitable value for a substituent on $R^2$ or for a substituent on Q when it is (1-6C)alkylamino, dialkylamino of up to 8 carbon atoms, fluoro-(1-3C)alkyl or phenyl-(1-3C)alkylamino is, for example, methylamino, ethylamino, propylamino, isopropylamino, butylamino, isobutylamino, sec-butylamino, tert-butylamino, pentylamino, isopentylamino, hexylamino, isohexylamino, 3-methylpentylamino, dimethylamino, diethylamino, dipropylamino, N-ethyl-N-methylamino, N-methy-N-propylamino, N-buty-N-methylamino, N-methyl-N-pentylamino, N-isopentyl-N-methylamino, N-hexy-N-methylamino, fluoromethyl, difluoromethyl, trifluoromethyl, 2,2,2-trifluoroethyl, 3,3,3-trifluoropropyl, benzylamino, phenethylamino or 3-phenylpropylamino.

A suitable value for Q when it is (1-6C)alkoxy is, for example, methoxy, ethoxy, propoxy, isopropoxy, butoxy, isobutoxy, sec-butoxy, tert-butoxy, pentyloxy or isopentyloxy.

A suitable value for Q when it is (1-10C)alkylamino or dialkylamino of up to 10 carbon atoms is, for example, methylamino, ethylamino, propylamino, isopropylamino, butylamino, isobutylamino, sec-butylamino, tert-butylamino, pentylamino, isopentylamino, hexylamino, isohexylamino, 3-methylpentylamino, 1-ethylpropylamino, 1-ethylpentylamino, 1,3-dimethylbutylamino, 1-ethyl-3-methylbutylamino, 1,4-dimethylpentylamino, 1-ethyl-4-methylpentylamino, dimethylamino, diethylamino, dipropylamino, N-ethyl-N-methylamino, N-methyl-N-propylamino, N-butyl-N-methylamino, N-methyl-N-pentylamino, N-isopentyl-N-methylamino or N-hexyl-N-methylamino.

A suitable value for Q when it is phenyl-(1-3C)alkylamino is, for example, benzylamino, phenethylamino or 3-phenylpropylamino.

A suitable value for a phenyl-(1-3C)alkyl substituent on Q is, for example, benzyl, phenethyl or 3-phenylpropyl.

Suitable values for substituents which may be present on a Phenyl or phenyl-(1-3C)alkylamino substituent on $R^2$, on a phenyl-(1-3C)-alkylamino, phenyl or phenyl-(1-3C)alkyl substituent on Q, or on the phenyl group when Q is phenyl-(1-3C)alkylamino, include the following, for example:

for halogeno: fluoro, chloro, bromo and iodo;
for (1-4C)alkyl: methyl, ethyl, propyl, isopropyl and butyl;
for (1-4C)alkoxy: methoxy, ethoxy, propoxy, isopropoxy and butoxy.

A suitable value for $R^2$ or for Q when it is (3-6C)-cycloalkylamino, N-alkyl-N-cycloalkylamino of up to 8 carbon atoms or dicycloalkylamino of up to 12 carbon atoms is, for example, cyclopropylamino, cyclobutylamino, cyclopentylamino, cyclohexylamino, N-cyclopentyl-N-methylamino, N-cyclohexyl-N-methylamino, dicylopentylamino or dicyclohexylamino.

A suitable value for a substituent on Q when it is (1-6C)alkyl is, for example, methyl, ethyl, propyl, isopropyl, butyl, isobutyl, pentyl or hexyl.

A suitable pharmaceutically-acceptable salt of the invention may be for those polypeptide compounds of the invention which are sufficiently basic (for example those which contain an Arg, D—Arg, Lys, D—Lys, His, D—His, MeHis, EtHis, PrHis, D—Ala(NH$_2$), His($\tau$Me) or His($\pi$-Me) group or those where the N-terminus is not acylated) an acid-addition salt and for those polypeptide compounds of the invention which are sufficiently acidic (for example those which contain a carboxy substituent or wherein $R^2$ is hydroxy) a base-addition salt.

A suitable pharmaceutically acceptable acid-addition salt of the invention may be formed with an inorganic acid, for example hydrochloric acid, hydrobromic acid, sulphuric acid or phosphoric acid, or with an organic acid, for example acetic acid, citric acid, maleic acid, fumaric acid, succinic acid, tartaric acid or trifluoroacetic acid.

Suitable pharmaceutically-acceptable base-addition salts of the invention include, for example, alkali metal (such as sodium or potassium), alkaline earth metal (such as calcium or magnesium), and ammonium salts, and salts with organic bases, for example salts with methylamine, dimethylamine and trimethylamine.

Particular groups of compounds of the invention include those polypeptide compounds of the formula I wherein:

(a) $R^1$ is pyrrolyl, indolyl, pyridyl, quinolyl, imidazolyl, pyrazolyl, pyrimidinyl, pyrazinyl or 1,2,4-triazolyl which may optionally bear one or two substituents selected from fluoro, chloro, methyl, methoxy, hydroxy and cyano; and $A^1$, $A^2$, $A^3$, $A^4$, $A^5$, $A^6$ and Q have any of the meanings defined hereinbefore;

(b) $A^1$ is a direct link to $A^2$, or is His, D—His, MeHis, EtHis, PrHis, D—Gln, D—Glu(OMe), Leu, MeLeu, Lys(CO-4-Pyridyl), Pal, D—Pal, Phe, Pro, His($\tau$-Me), His($\pi$-Me) or Trp; and $R^1$, $A^2$, $A^3$, $A^4$, $A^5$, $A^6$ and Q have any of the meanings defined hereinbefore;

(c) $A^1$ is His, D—His, D—Gln, D—Glu(OMe), Leu, Pal, D—Pal, Phe, Pro, His($\tau$-Me) or His($\pi$-Me); and $R^1$, $A^2$, $A^3$, $A^4$, $A^5$, $A^6$ and Q have any of the meanings defined hereinbefore;

(d) $A^2$ is Trp, MeTrp, Trp(Me), Trp(For), L—Nal, pcF, Lys or Pal; and $R^1$, $A^1$, $A^3$, $A^4$, $A^5$, $A^6$ and Q have any of the meanings defined hereinbefore;

(e) $A^2$ is Trp or MeTrp; and $R^1$, $A^1$, $A^3$, $A^4$, $A^5$, $A^6$ and Q have any of the meanings defined hereinbefore;

(f) $A^3$ is Ala, MeAla, Aib, Gly, Leu, Ser, Val or Thr; and $R^1$, $A^1$, $A^2$, $A^4$, $A^5$, $A^6$ and Q have any of the meanings defined hereinbefore;

(g) $A^3$ is Ala or MeAla; and $R^1$, $A^1$, $A^2$, $A^4$, $A^5$, $A^6$ and Q have any of the meanings defined hereinbefore;

(h) $A^4$ is Val, Aib, Leu, Ile or Thr; and $R^1$, $A^1$, $A^2$, $A^3$, $A^5$, $A^6$ and Q have any of the meanings defined hereinbefore;

(i) $A^4$ is Val; and $R^1$, $A^1$, $A^2$, $A^3$, $A^5$, $A^6$ and Q have any of the meanings defined hereinbefore;

(j) $A^5$ is Gly, Sar, D—Ala, D—Ser, D—Ser(CH$_2$Ph), D—pcF, Aib, D—Pro or D—Lys; and $R^1$, $A^1$, $A^2$, $A^3$, $A^4$, $A^6$ and Q have any of the meanings defined hereinbefore;

(k) $A^5$ is Gly, Sar, D—Ala, D—Ser, D—Ser(CH$_2$Ph), D—pcF, Aib or D—Pro; and $R^1$, $A^1$, $A^2$, $A^3$, $A^4$, $A^6$ and Q have any of the meanings defined hereinbefore;

(l) $A^6$ is His, MeHis, His($\tau$-Me), His($\pi$-Me), Val, Leu, Pro, Phe, Gln, Lys(Z), Lys(COCH$_3$), Lys(COPh), Lys(COCH$_2$Ph), Lys(COCH$_2$CH$_2$Ph), Pal, Ser, Ser(CH$_2$Ph), Thr, Thr(CH$_2$Ph), Trp or L—Nal; and $R^1$, $A^1$, $A^2$, $A^3$, $A^4$, $A^5$ and Q have any of the meanings defined hereinbefore;

(m) $A^6$ is His, MeHis, His($\tau$-Me), His($\pi$-Me), Leu, Pro, Phe, Gln, Lys, Lys(Z) or Pal; and $R^1$ $A^1$ $A^2$ $A^3$ $A^4$ $A^5$ and Q have any of the meanings defined hereinbefore;

(n) Q is a group of the formula —$A^7.R^2$ in which $A^7$ is Leu, D—Leu, MeLeu, Ile, MeIle, Ahx, Aib, Val, MeVal, Phe, Ape or Met and $R^2$ is hydroxy or amino; or $R^2$ is (1-3C)alkylamino, dialkylamino of up to 4 carbon atoms or (1-3C)alkoxy, each optionally bearing an amino, (1-6C)alkylamino or phenyl-(1-3C)alkylamino substituent, other than in a position alpha to an oxygen or nitrogen atom, or a fluoro-(1-3C)alkyl or phenyl substituent; and $R^1$, $A^1$, $A^2$, $A^3$, $A^4$, $A^5$ and $A^6$ have any of the meanings defined hereinbefore;

(o) Q is a group of the formula —$A^7.R^2$ in which $A^7$ is Leu, MeLeu, Ile, Ahx, Val or Phe and $R^2$ is methoxy, amino, methylamino or dimethylamino, each optionally bearing a trifluoromethyl or phenyl substituent, or $R^2$ is ethoxy or ethylamino, each optionally bearing an amino, methylamino, ethylamino, isobutylamino, isopentylamino, benzylamino or phenethylamino substituent, other than in a position alpha to an oxygen or nitrogen atom, or a trifluoromethyl or phenyl substituent; and $R^1$, $A^1$, $A^2$, $A^3$, $A^4$, $A^5$ and $A^6$ have any of the meanings defined hereinbefore;

(p) Q is a group of the formula $A^7.R^2$ in which $A^7$ is Leu, D—Leu, MeLeu, Ile, MeIle, Ahx, Aib, Val, MeVal, Phe, Ape or Met and $R^2$ is (3-6C)cycloalkylamino, or $R^2$ is 1-pyrrolidinyl, piperidino, morpholino or 1-piperazinyl; and $R^1$, $A^1$, $A^2$, $A^3$, $A^4$, $A^5$ and $A^6$ have any of the meanings defined hereinbefore;

(q) Q is a group of the formula —$A^7.R^2$ in which $A^7$ is Leu, MeLeu, Ile, Ahx, Val or Phe and $R^2$ is cyclopentylamino or 1-pyrrolidinyl; and $R^1$, $A^1$, $A^2$, $A^3$, $A^4$, $A^5$ and $A^6$ have any of the meanings defined hereinbefore;

(r) Q is (1-6C)alkoxy, (1-10)alkylamino or dialkylamino of up to 10 carbon atoms, each optionally bearing an amino, (1-6C)alkylamino or phenyl-(1-3C)alkylamino substituent, other than in a position alpha to an oxygen or nitrogen atom, or a phenyl substituent; or Q is phenyl-(1-3C)alkylamino; and wherein within Q a phenyl group may optionally bear a substituent selected from chloro, methyl, methoxy and hydroxy and $R^1$, $A^1$, $A^2$, $A^3$, $A^4$, $A^5$ and $A^6$ have any of the meanings defined hereinbefore;

(s) Q is methoxy, isopropoxy, isobutoxy, isopentyloxy, methylamino, isobutylamino, isopentylamino, 1-ethylpropylamino or 1,3-dimethylbutyamino, each optionally bearing an amino, methylamino, isopropylamino, isobutylamino, isopentylamino, benzylamino or phenethylamino substituent, other than in a position alpha to an oxygen or nitrogen atom, or a phenyl substituent, or Q is benzylamino or phenethylamino; and $R^1$, $A^1$, $A^2$, $A^3$, $A^4$, $A^5$ and $A^6$ have any of the meanings defined hereinbefore;

(t) Q is (3-6C)cycloalkylamino, or Q is 1-pyrrolidinyl, piperidino, morpholino or 1-piperazinyl, each optionally bearing on any available position, including on any available nitrogen atom, a substituent selected from (1-6C)alkyl, phenyl and phenyl-(1-3C)alkyl; and wherein within Q a phenyl group may optionally bear a substituent selected from chloro, methyl, methoxy and hydroxy; and RI, $A^1$, $A^2$, $A^3$, $A^4$, $A^5$ and $A^6$ have any of the meanings defined hereinbefore; and (u) Q is cyclopentylamino, cyclohexylamino, piperidino, 4-phenylpiperidino, morpholino or 4-benzylpiperazin-1-yl; and $R^1$, $A^1$, $A^2$, $A^3$, $A^4$, $A^5$ and $A^6$ have any of the meanings defined hereinbefore; together in each group with a pharmaceutically-acceptable salt of each polypeptide compound.

A further particular group of compounds of the invention comprises polypeptide compounds of the formula I wherein $R^1$ is pyrrolyl, indolyl, pyridyl, quinolyl, imidazolyl, pyrazolyl, pyrimidinyl, pyrazinyl or 1,2,4-triazolyl which may optionally bear one or two substituents selected from fluoro, chloro, methyl, methoxy, hydroxy and cyano;

wherein $A^1$ is a direct link to $A^2$, or is His, D—His, MeHis, EtHis, PrHis, D—Gln, Glu(OMe), Leu, MeLeu, Lys(CO-4-Pyridyl), Pal, D—Pal, Phe, Pro, His($\tau$-Me), His($\pi$-Me) or Trp;

wherein $A^2$ is Trp, MeTrp, Trp(Me), Trp(For), L—Nal, pcF or Pal;

wherein $A^3$ is Ala, MeAla, Gly, Leu, Ser, Val or Thr;

wherein $A^4$ is Val, Aib, Leu, Ile or Thr;

wherein $A^5$ is Gly, Sar, D—Ala, D—Ser, D—Ser(CH$_2$Ph), D—pcF, Aib, D—Pro or D—Lys;

wherein $A^6$ is His, MeHis, His($\pi$-Me), His(x Me), Val, Leu, Pro, Phe, Gln, Lys(Z), Lys(COCH$_3$), Lys(COPh), Lys(COCH$_2$Ph), Lys(COCH$_2$CH$_2$Ph), Pal, Ser, Ser(CH$_2$Ph), Thr, Thr(CH$_2$Ph), Trp or L—Nal; and wherein Q is a group of the formula —$A^7$.$R^2$ in which $A^7$ is Leu, D—Leu, MeLeu, Ile, MeIle, Ahx, Aib, Val, MeVal, Phe, Ape or Met and $R^2$ is hydroxy or amino; or $R^2$ is (1-3C)alkylamino (especially methylamino and ethylamino), dialkylamino of up to 4-carbon atoms (especially dimethylamino and N-ethyl-N-methylamino) or (1-3C)alkoxy (especially methoxy and ethoxy), each optionally bearing an amino, (1-6C)alkylamino (especially methylamino, ethylamino, isobutylamino and isopentylamino) or phenyl-(1-3C)alkylamino (especially benzylamino and phenethylamino) substituent, other than in a position alpha to an oxygen or nitrogen atom, or a fluoro-(1-3C)alkyl (especially trifluoromethyl) or phenyl substituent; or $R^2$ is (3-6C)cycloalkylamino (especially cyclopentylamino and cyclohexylamino); or $R^2$ is 1-pyrrolidinyl, piperidino, morpholino or 1-piperazinyl;

or Q is (1-6C)alkoxy (especially methoxy, isopropoxy, isobutoxy, tert-butoxy and isopentyloxy), (1-10C)alkylamino (especially methylamino, isobutylamino, isopentylamino, 1-ethylpropylamino, 1-ethylpentylamino, 1,3-dimethylbutyamino and 1,4 dimethylpentylamino) or dialkylamino of up to 10 carbon atoms (especially dimethylamino, N-ethyl-N-methylamino and N-isopentyl-N-methylamino), each optionally bearing an amino, (1-6C)alkylamino (especially methylamino, isopropylamino, isobutylamino and isopentylamino) or phenyl-(1-3C)alkylamino (especially benzylamino and phenethylamino) substituent, other than in a position alpha to an oxygen or nitrogen atom, or a phenyl substituent; or Q is phenyl-(1-3C)alkylamino (especially benzylamino and phenethylamino); or Q is (3-6C)cycloalkylamino (especially cyclopentylamino and cyclohexylamino); or Q is 1-pyrrolidinyl, piperidino, morpholino or 1-piperazinyl, each optionally bearing on any available position, including on any available nitrogen atom, a substituent selected from (1-6C)alkyl (especially methyl and ethyl), phenyl and phenyl-(1-3C)alkyl (especially benzyl and phenethyl); and wherein within Q a phenyl group may optionally bear a substituent selected from chloro, methyl, methoxy and hydroxy; and the pharmaceutically-acceptable salts thereof.

Another particular group of compounds of the invention comprises polypeptide compounds of the formula I wherein $R^1$ is 2-pyrrolyl, 2-indolyl, 3-indolyl, 2-pyridyl, 3-pyridyl, 4-pyridyl, 2-imidazolyl, 4-pyrazolyl, 2-pyrimidinyl, 4-pyrimidinyl, 5-pyrimidinyl or 2-pyrazinyl which may optionally bear a substituent selected from chloro, methyl, methoxy, hydroxy or cyano;

$A^1$ is His, D—His, D—Gln, D—Glu(OMe), Leu, Pal, D—Pal, Phe, Pro, His($\tau$-Me) or His($\pi$-Me);

$A^2$ is Trp or MeTrp; $A^3$ is Ala, MeAla or Aib; $A^4$ is Val;

$A^5$ is Gly, Sar, D—Ala, D—Ser, D—Ser(CH$_2$Ph), D—pcF, Aib or D—Pro;

$A^6$ is His, MeHis, His($\tau$-Me), His($\pi$Me), Leu, Pro, Phe, Gln, Lys, Lys(Z) or Pal; and Q is a group of the formula —$A^7$.$R^2$ in which $A^7$ is Leu, MeLeu, Ile, Ahx, Val or Phe and $R^2$ is methoxy, amino or methylamino, each optionally bearing a trifluoromethyl or phenyl substituent, or $R^2$ is ethoxy or ethylamino, each optionally bearing an amino, methylamino, ethylamino, isobutylamino, isopentylamino, benzylamino or phenethylamino substituent, other than in a position alpha to an oxygen or nitrogen atom, or a trifluoromethyl or phenyl substituent;

or $R^2$ is cyclopentylamino or 1-pyrrolidinyl;

or Q is methoxy, isopropoxy, isobutoxy, isopentyloxy, methylamino, isobutylamino, isopentylamino, 1-ethylpropylamino or 1,3-dimethylbutylamino, each optionally bearing an amino, methylamino, isopropylamino, isobutylamino, isopentylamino, benzylamino or phenethylamino substituent, other than in a position alpha to an oxygen or nitrogen atom, or a phenyl substituent, or Q is benzylamino or phenethylamino;

or Q is cyclopentylamino, cyclohexylamino, piperidino, 4-phenylpiperidino, morpholino or 4-benzylpiperazin-1-yl; and the pharmaceutically-acceptable acid-addition salts thereof.

Another particular group of compounds of the invention comprises polypeptide compounds of the formula I wherein $R^1$ is 2-pyrrolyl, 2-indolyl, 3-indolyl, 2-pyridyl, 3-pyridyl, 4-pyridyl, 2-imidazolyl, 4-pyrazolyl, 2-pyrimidinyl, 4-pyrimidinyl, 5-pyrimidinyl or 2-pyrazinyl which may optionally bear a substituent selected from chloro, methyl, methoxy, hydroxy or cyano;

$A^1$ is a direct link to $A^2$, or is His, D—His, D—Gln, D—Glu(OMe), Leu, MeLeu, Lys(Co-4-Pyridyl), Pal, D—Pal, Phe, Pro, His($\tau$-Me) or His($\pi$-Me);

$A^2$ is Trp or MeTrp; $A^3$ is Ala, MeAla or Ser; $A^4$ is Val or Ile;

$A^5$ is Gly, Sar, D—Ala, D—Ser, D—Ser($CH_2Ph$), D—pcF, Aib or D—Pro;

$A^6$ is His, MeHis, His($\tau$-Me), His($\pi$-Me), Val, Leu, Pro, Phe, Gln, Lys(Z), Lys($COCH_3$), Lys(COPh), Lys($COCH_2Ph$), Lys($COCH_2CH_2Ph$), Pal, L Ser, Ser($CH_2Ph$), Thr, Thr($CH_2Ph$), Trp or L Nal; and Q is a group of the formula —$A^7.R^2$ in which $A^7$ is Leu, HeLeu, Ile, Ahx, Val or Phe and $R^2$ is methoxy, amino or methylamino, each optionally bearing a trifluoromethy or phenyl substituent, or $R^2$ is ethoxy or ethylamino, each optionally bearing an amino, methylamino, ethylamino, isobutylamino, isopentylamino, benzylamino or phenethylamino substituent, other than in a position alpha to an oxygen or nitrogen atom, or a trifluoromethyl or phenyl substituent;

or $R^2$ is cyclopentylamino or 1-pyrrolidinyl;

or Q is methoxy, isopropoxy, isobutoxy, isopentyloxy, methylamino, isobutylamino, isopentylamino, 1-ethylpropylamino or 1,3-dimethylbutylamino, each optionally bearing an amino, methylamino, isopropylamino, isobutylamino, isopentylamino, benzylamino or phenethylamino substituent, other than in a position alpha to an oxygen or nitrogen atom, or a phenyl substituent, or Q is benzylamino or phenethylamino;

or Q is cyclopentylamino, cyclohexylamino, piperidino, 4-phenylpiperidino, morpholino or 4-benzylpiperazin-1-yl; and the pharmaceutically-acceptable acid-addition salts thereof.

Another particular group of compounds of the invention comprises polypeptide compounds of the formula I wherein $R^1$ is 2-pyrrolyl, 2-indolyl, N-methylindol-2-yl, 3-indolyl, 2-pyridyl, 3-pyridyl, 4-pyridyl, 2-chloropyrid-3-yl, 6-chloropyrid-3-yl, 6-methylpyrid-3-yl, 4-pyrazolyl or 2-pyrazinyl;

$A^1$ is His, D—His, D—Gln, D—Glu(OMe), Leu, Lys(CO-4-Pyridyl), Pro, His($\tau$-Me) or His($\pi$-Me);

$A^2$ is Trp; $A^3$ is Ala or Ser; $A^4$ is Val;

$A^5$ is Gly, Sar or D—Ala; $A^6$ is His, Leu, Phe, Gln, Lys(Z), Lys($COCH_3$), Lys($COCH_2Ph$) or Lys($COCH_2CH_2Ph$); and Q is a group of the formula —$A^7.R^2$ in which $A^7$ is Leu, MeLeu, Ile or Val and $R^2$ is methoxy, amino, methylamino, ethylamino or dimethylamino;

and the pharmaceutically-acceptable salts thereof.

A preferred group of compounds of the invention comprises polypeptide compounds of the formula I wherein $R^1$ is 3-pyridyl, 4-pyridyl, 2-pyrazinyl, 2-indolyl or 3-indolyl;

$A^1$ is His;

$A^2$ is Trp; $A^3$ is Ala; $A^4$ is Val;

$A^5$ is D—Ala; $A^6$ is His, Lys(Z), Lys($COCH_3$), Lys($COCH_2Ph$) or Lys($COCH_2CH_2Ph$); and Q is a group of the formula —$A^7.R^2$ in which $A^7$ is Leu or MeLeu and $R^2$ is methoxy or methylamino;

and the pharmaceutically acceptable salts thereof.

Specific preferred compounds of the invention include, for example, the following polypeptides of formula I:

4-pyridyl—CO—His—Trp—Ala—Val—N—Ala—His—Leu—OMe and
4-pyridyl—CO—His—Trp—Ala—Val—N—Ala—His—Leu—NHMe.

Further specific preferred compounds of the invention include, for example, the following polypeptides of formula I:

4-Pyridyl—CO—His—Trp—Ala—Val—D—Ala—His—MeLeu—OMe,
3-Pyridyl—CO—His—Trp—Ala—Val—D—Ala—His—MeLeu—OMe,
4-Pyridyl—CO—His—Trp—Ala—Val—D—Ala—Lys(Z) MeLe-OMe,
3-Indolyl—CO—His—Trp—Ala—Val—D—Ala—His—Leu—OMe,
4-Pyridyl—CO—His—Trp—Ala—Val—D—Ala—His—HeLeu—NHMe
4-Pyridyl-CO His—Trp—Ala—Val—N—Ala—Lys(Z)—Leu—NHMe,
4-Pyridyl-CO His—Trp—Ala—Val—N-Ala-Lys($COCH_2Ph$) Leu—NHMe and
4-Pyridyl—CO—His—Trp—Ala—Val—N—Ala—Lys($COCH_2CH_2Ph$) Leu—NHMe.

The invention provides, as a further feature, any one or more of the preferred compounds together with their pharmaceutically acceptable acid-addition salts.

The polypeptide of the invention may be prepared by any process well known in the art of peptide chemistry to be applicable to the synthesis of analogous compounds. Thus, for example, a polypeptide of the invention may be obtained by procedures analogous to those disclosed in "Solid Phase Peptide Synthesis" by Stewart and Young (published by the Pierce Chemical Company, Illinois, 1984), "Principles of Peptide Synthesis" (published by Springer-Verlag, Berlin, 1984) and "Practice of Peptide Synthesis" (published by Springer-Verlag, Berlin, 1984).

Preferred processes for the manufacture of a polypeptide of the invention include, for example:

(a) the removal of one or more conventional peptide protecting groups from a protected polypeptide to give a polypeptide of the invention of formula I;

(b) the formation of an amide bond by coupling two peptide units, one containing a carboxylic acid group, or a reactive derivative thereof, and the other containing an amino group, such that a protected or unprotected polypeptide having the sequence indicated in formula I is produced whereafter, if necessary, the protecting groups are removed using process (a) above;

(c) for the manufacture of a polypeptide of the invention wherein $R^1$ is a 5- or 6-membered unsaturated heterocyclic ring as defined above, the reaction of a protected or unprotected polypeptide having the sequence indicated in formula I wherein the group $R^1$—CO— is hydrogen with the appropriate acylating agent in the presence, if necessary, of a suitable base whereafter, if necessary, the protecting groups are removed using process (a) above;

(d) for the manufacture of a polypeptide of the invention wherein $R^2$ is (1-3C)alkoxy or Q is (1-6C)alkoxy, each optionally substituted as stated above, the esterification of a protected or unprotected polypeptide having the sequence indicated in formula I wherein $R^2$ or Q is hydroxy, or a reactive derivative thereof, with the appropriate alcohol, whereafter, if necessary, the protecting groups are removed using process (a) above;

(e) for the manufacture of a polypeptide of the invention wherein $R^2$ is amino, (1-3C)alkylamino or dialkylamino of up to 4-carbon atoms, or Q is (1-10C)alkylamino, dialkylamino of up to 10 carbon atoms or phenyl-(1-3C)alkylamino each optionally substituted as stated above; or $R^2$ or Q is (3-6C)cycloalkylamino, N-alkyl-N-cycloalkylamino of up to 8 carbon atoms or dicycloalkylamino of up to 12 carbon atoms; or $R^2$ is 1-pyrrolidinyl, piperidino, morpholino, 1-piperazinyl or 4-methylpiperazin-1-yl; or Q is 1-azirinyl, 1-azetidinyl, 1-pyrrolidinyl, piperidino, morpholino, 1-piperazinyl or 1-homopiperidinyl each optionally substituted as stated above, the reaction of a protected or unprotected polypeptide having the sequence indicated in formula I wherein $R^2$ or Q is hydroxy, or a reactive derivative thereof, or (1-6C)alkoxy, with ammonia, with the appropriate alkylamine, dialkylamine or phenylalkylamine, with the appropriate cycloalkylamine, N-alkyl-N-cycloalkylamine or dicycloalkylamine, or with the appropriate heterocycle whereafter, if necessary, the protecting groups are removed using process (a) above; and (f) for the manufacture of a polypeptide of the invention wherein $R^2$ is hydroxy, the hydrolysis of the protected or unprotected polypeptide having the sequence indicated in formula I wherein $R^2$ is (1-3C)alkoxy whereafter, if necessary, the protecting groups are removed using process (a) above.

In process (a) there may be as many protecting groups in the starting material as there are radicals which may require protection, for example some or all of those groups which exist in the product as free hydroxy groups or basic amino groups (whether primary or secondary amino groups). The protecting group or groups may be chosen from those described in the standard text books on peptide chemistry stated above. Various methods for the removal of the protecting group or groups are also described in those books.

In process (a) a suitable protecting group for a basic amino group (whether at the N-terminus or in an amino acid side chain) is, for example, an arylmethoxycarbonyl group, for example a Z—, Z(NO$_2$)—, Z(Br)—, Z(Cl)— or Z(OMe)— group, which may be removed by hydrogenation over a catalyst, for example palladium-on-charcoal or it may be removed by treatment with an inorganic acid, for example anhydrous hydrogen fluoride or hydrogen bromide.

In process (a) a particularly suitable protecting group for a basic amino group is, for example, an alkoxycarbonyl group, for example a Boc-group, which may be removed by treatment with an organic acid, for example trifluoroacetic acid, or it may be removed by treatment with an inorganic acid, for example anhydrous hydrogen chloride or hydrogen bromide; or for example a 9-fluorenylmethoxycarbonyl group, which may be removed by treatment with an organic base, for example piperidine.

In process (a) a particularly suitable protecting group for the basic amino group in the side chain of Histidine is, for example, an arylsulphonyl group, for example a tosyl group, which may be removed by treatment with a hydroxylamine, for example an N-hydroxytriazole, particularly 1-hydroxybenzotriazole.

In process (a) a suitable protecting group for a hydroxy group is, for example, an arylmethyl group, for example a benzyl group, which may be removed by treatment with an inorganic acid, for example anhydrous hydrogen fluoride, or it may be removed by hydrogenation over a catalyst, for example palladium-on-charcoal; or it may be for example, an esterifying group, for example an acetyl or benzoyl group, which may be removed by hydrolysis with a base, for example sodium hydroxide.

In process (a) a suitable protecting group for a carboxy group is, for example, an esterifying group, for example an arylmethyl group, for example a benzyl group, which may be removed by treatment with an inorganic acid, for example anhydrous hydrogen fluoride, or it may be removed by hydrogenation over a catalyst, for example palladium-on-charcoal; or, for example a tert butyl group which may be removed by treatment with an organic acid, for example trifluoroacetic acid.

In process (a) particularly suitable protection for a carboxy group at the C-terminus is afforded by the formation of, for example, an ester, for example the ester formed by the coupling of the C-terminus amino acid and a resin, for example a hydroxymethylated styrene-divinylbenzene crosslinked resin; or by the formation of, for example, an amide, for example the amide formed by the coupling of the C-terminus amino acid and a resin, for example a methylbenzhydrylamine styrene-divinylbenzene crosslinked resin.

In process (b) any one of the standard peptide coupling reactions may be used, for example those described in the standard text books on peptide chemistry stated above.

In process (b) it is to be understood that a peptide unit may contain just one protected or unprotected amino acid.

In process (b) a suitable coupling reaction is, for example, a solution-phase coupling reaction, for example an active ester coupling, an azide coupling or a coupling involving N/ '-dicyclohexylcarbodiimide and 1-hydroxybenzotriazole.

In process (b) a suitable reactive derivative of the peptide unit containing a carboxylic acid group is, for example, an acyl halide, for example an acyl chloride formed by the reaction of the acid and an inorganic acid chloride, for example thionyl chloride; a mixed anhydride, for example an anhydride formed by the reaction of the acid and a haloformate, for example isobutyl chloroformate; or an acyl azide, for example an azide formed by the reaction of the acid and an azide such as diphenylphosphoryl azide.

In process (b) a particularly suitable reactive derivative of the peptide unit containing a carboxylic acid group is, for example, the product of the reaction of the acid and a carbodiimide, for example N/ '-dicyclohexylcarbodiimide or N/ '-diisopropylcarbodiimide, or it is the product of the reaction of the acid, an N-hydroxytriazole, for example 1-hydroxybenzotriazole, and a carbodiimide, for example N '-dicyclohexylcarbodiimide or N '-diisopropylcarbodiimide.

In process (b) a preferred strategy is, for example, to use a solid-phase synthesis wherein the amino acid which is to become the C̱-terminus amino acid of a polypeptide of the invention is protected at the alpha amino group and, if necessary, in the side-chain and coupled to a solid support, for example a resin, for example a hydroxymethylated or a methylbenzhydrylamine styrene-divinylbenzene crosslinked resin via an ester or amide linkage respectively, whereafter the protecting group on the alpha-amino group is removed. The amino acid which is to be attached to the C̱-terminus amino acid is protected at the alpha-amino group and, if necessary, in the side-chain and coupled to the C̱-terminus amino acid which remains attached to the solid support. The step-wise process of deprotection of the alpha-amino group and coupling to the next amino acid is repeated to give a protected or unprotected polypeptide attached to the solid support.

The protected or unprotected polypeptide may be released from the hydroxymethylated resin solid support by, for example, hydrolysis, for example acid hydrolysis with, for example, an organic acid, for example trifluoroacetic acid or with, for example, an inorganic acid, for example anhydrous hydrogen fluoride or hydrogen bromide; or the polypeptide is released by, for example, alcoholysis, for example methanolysis, in the presence of a base, for example an organic base, for example diisopropylethylamine whereafter, if necessary, the protecting groups are removed using process (a) above.

When a methylbenzhydrylamine resin is used, the protected or unprotected polypeptide may be released from the solid support, for example, by treatment with an inorganic acid, for example hydrogen fluoride, whereafter, if necessary, the protecting groups are removed using process (a) above.

In process (b) a further preferred strategy is, for example, to use a solid-phase synthesis wherein an amino acid which is to become a link within the chain of amino acids forming a polypeptide of the invention is protected at the alpha-amino group and, if necessary, in the side-chain and coupled to a solid support, for example a resin as described above, whereafter the protecting group on the alpha-amino group is removed. The amino acid which is to be attached to the amino acid which has been coupled to the solid support is protected at the alpha-amino group and, if necessary, in the side-chain and coupled to the amino acid which remains coupled to the solid support. The step-wise process of deprotection of the alpha-amino group and coupling to the next amino acid is repeated to give a protected or unprotected polypeptide attached to the solid support.

The protected or unprotected polypeptide may be released from the solid support, for example, using one of the methods described above whereafter a further peptide unit can be coupled using a solution-phase coupling reaction as described for process (b) above, and whereafter, if necessary, the protecting groups are removed using process (a) above.

In process (c) a suitable acylating agent is, for example, a 5- or 6-membered unsaturated heterocyclic ring carboxylic acid anhydride, or a mixed anhydride, for example an anhydride formed by the reaction of a 5- or 6-membered unsaturated heterocyclic ring carboxylic acid with a haloformate, for example isobutyl chloroformate.

In process (c) a further suitable acylating agent is, for example, an acyl halide, for example a 5- or 6-membered unsaturated heterocyclic ring carbonyl halide, for example a 5- or 6-membered unsaturated heterocyclic ring carbonyl chloride or bromide, in the presence of a suitable base, for example an organic base, for example pyridine, 4-dimethylaminopyridine or triethylamine, or an inorganic base, for example potassium carbonate or sodium acetate.

In process (c) a particularly suitable acylating agent is, for example, the product of the reaction of a 5- or 6-membered unsaturated heterocyclic ring carboxylic acid and a carbodiimide, for example Ṉ/'-dicyclohexylcarbodiimide or Ṉ/'-diisopropylcarbodiimide, or it is the product of the reaction of the carboxylic acid, an Ṉ-hydroxybenzotriazole, for example 1-hydroxybenzotriazole, and a carbodiimide, for example Ṉ/'-dicyclohexylcarbodiimide or Ṉ/'-diisopropylcarbodiimide.

In processes (d) and (e) a suitable reactive derivative of the acid of formula I wherein $R^2$ or Q is hydroxy is, for example, the corresponding acyl halide, for example the acyl chloride formed by the reaction of the acid with an inorganic acid chloride, for example thionyl chloride; the corresponding mixed anhydride, for example the anhydride formed by the reaction of the acid with a haloformate, for example isobutyl chloroformate; or the corresponding ester, for example the ester formed at the end of the step-wise process described above as a preferred strategy for carrying out process (b).

In process (d) suitable esterification conditions are, for example, to react the acid of formula I wherein $R^2$ or Q is hydroxy with a (1-3C)alcohol or a (1-6C)alcohol respectively in the presence of suitable coupling agents, for example a carbodiimide, for example Ṉ/'-dicyclohexylcarbodiimide or Ṉ/'-diisopropylcarbodiimide, and an organic amine, for example a pyridine, for example 4-dimethylaminopyridine.

In process (d) particularly suitable conditions are, for example, to react the reactive derivative of the acid of formula I wherein $R^2$ or Q is hydroxy comprising the ester formed by the coupling of the acid and the hydroxymethylated resin with the appropriate alcohol, for example a (1-6C)alcohol, in the presence of a suitable base, for example an organic base, for example diisopropylethylamine.

In process (e) particularly suitable conditions are, for example, to react the ester of formula I wherein $R^2$ is (1-3C)alkoxy or Q is (1-6C)alkoxy with ammonia, with the appropriate alkylamine, dialkylamine or phenylalkylamine, with the appropriate cycloalkylamine, Ṉ-alkyl-Ṉ-cycloalkylamine or dicycloalkylamine, or with the appropriate heterocycle in the presence of a diluent or solvent, for example ethanol or tetrahydrofuran.

In process (f) the ester of formula I wherein $R^2$ is (1-3C)alkoxy may be hydrolysed, for example with a base, for example sodium hydroxide in the presence of a diluent or solvent, for example methanol.

The above processes may be carried out analogously to those described in the accompanying examples. The starting materials for use in the processes of the invention which are not particularly described therein are either known compounds or may be produced and purified by methods well known to one skilled in the art.

As stated above polypeptide compounds of the invention possess bombesin antagonist properties. This activity may be demonstrated, for example, using one or more of the procedures set out below:

(a) An in vitro binding assay which assesses the ability of a test compound to displace radiolabelled gastrin releasing peptide ([I$^{125}$]GRP) from the bombesin receptor of mouse Swiss 3T3-fibroblast cells. The test is similar to that described by I. Zachary and E. Rozengurt, *Proc. Nat. Acad. Sci. USA*, 1985, 82, 7616, except that the cells are incubated at ambient temperature for 1 hour;

(b) An in vitro assay which assesses the ability of a test compound to inhibit the Neuromedin C stimulated mitogenesis of mouse Swiss 3T3-fibroblast cells as determined by the uptake of [$^3$H]-thymidine. The test is similar to those described by N. Corps., L. Rees and K. Brown, *Biochem. Journal*, 1985, 231, 781 and I. Zachary and E. Rozengurt, *Proc. Nat. Acad. Sci. USA*, 1985, 82, 7616, except that GRP (18-27) (0.2 or 0.4nM) was used to stimulate growth and the test compounds were dissolved in an assay medium containing 0.1% bovine serum albumin and 0.4% dimethylsulphoxide and (c) An in vivo test involving the measurement of the antagonism of the bombesin-induced stimulation of the secretion of the enzyme amylase into the pancreatic duct of the rat by a test compound administered orally, sub-cutaneously or intravenously. Bombesin and the test compound can be administered concomitantly or the test compound can be predosed at any convenient interval, for example 30, 60, 90, 120, 150 or 180 minutes, before bombesin is dosed. Amylase was measured by analysis of the conversion of starch into maltose, on incubation of the starch/amylase mixture at 30° C. for 15 minutes, using a spectrophotometric assay as originally described by P. Bernfield in 'Methods in Enzymology' Vol. I, p17 (Editors Colowick and Kaplan, Academic Press, New York, 1955). Bombesin (5 micrograms/kg, intravenously) causes a large, but submaximal, increase of amylase secretion within 30 minutes.

Although the pharmacological properties of the polypeptide compounds of formula I vary with structural changes, in general polypeptide compounds of formula I possess bombesin antagonist properties at the following concentrations or doses in one or more of the above tests (a) to (c):

| | |
|---|---|
| Test (a) | IC$_{50}$ in the range, for example, 0.01–1000 nM; |
| Test (b) | IC$_{50}$ in the range, for example, 0.01 nM to 5 microM; and |
| Test (c) | IC$_{50}$ in the range, for example 5 micrograms/kg to 10 mg/kg intravenously or 5 micrograms/kg to 20 mg/kg sub-cutaneously. |

Thus, by way of example, the polypeptide 4-Pyridyl—CO—His—Trp—Ala—Vla—N—Ala—His—Leu—OMe has an IC$_{50}$ of 1.5 nM in test (a); an IC$_{50}$ of 0.7 nM in test (b); and an IC$_{50}$ of <0.5 mg/kg sub-cutaneously when dosed 150 minutes before bombesin in test (c); and the polypeptide 4-Pyridyl—CO—His—Trp—Ala—Val—N—Ala—Lys(-Z)—Leu—NHMe has an IC$_{50}$ of 0.2 nM in test (b); and an IC$_{50}$ of <0.02 mg/kg sub-cutaneously when dosed 150 minutes before bombesin in test (c).

In general those polypeptide compounds of formula I which are especially preferred have an IC$_{50}$ in the range 0.01 to 100 nM in test (a), an IC$_{50}$ in the range 0.01 to 100 nM in test (b) and an IC$_{50}$ in the range 5 micrograms/kg to 1 mg/kg intravenously in test (c).

No overt toxicity or other untoward effects are present in test (c) when polypeptide compounds of formula I are administered at several multiples of their minimum inhibitory dose.

According to a further feature of the invention there is provided a pharmaceutical composition which comprises a polypeptide of formula I, or a pharmaceutically acceptable salt thereof, in association with a pharmaceutically acceptable diluent or carrier.

The composition may be in a form suitable for oral use, for example a tablet, capsule, aqueous or oily solution, suspension or emulsion; for nasal use, for example a snuff, nasal spray or nasal drops; for vaginal or rectal use, for example a suppository; for administration by inhalation, for example as a finely divided powder or a liquid aerosol; for sub-linqual or buccal use, for example a tablet or capsule; or for parenteral use (including intravenous, subcutaneous, intramuscular, intravascular or infusion), for example a sterile aqueous or oily solution or suspension.

In general the above compositions may be prepared in a conventional manner using conventional excipients. However, in the case of a composition for oral administration, it may be convenient for the composition to include a coating to protect the polypeptide active ingredient from the actions of enzymes in the stomach.

A composition of the invention may also contain, in antitumour substances selected from, for example, mitotic inhibitors, for example vinblastine; alkylating agents, for example cis-platin, carboplatin and cyclophosphamide; antimetabolites, for example, 5-fluorouracil, cytosine arabinoside and hydroxyurea; intercalating antibiotics, for example adriamycin and bleomycin; enzymes, for example asparaginase; topoisomerase inhibitors, for example etoposide and biological response modifiers, for example interferon.

A preferred composition of the invention is, for example, one suitable for oral administration in unit dosage form, for example a tablet or capsule which contains from 2.5 to 500 mg, and preferably 10 to 100 mg, of polypeptide in each unit dose, or one suitable for parenteral administration which contains from 0.5 to 100 mg of polypeptide per ml, and preferably 1 to 10 mg of polypeptide per ml of solution.

A parenteral composition is preferably a solution in isotonic saline or isotonic dextrose buffered if necessary to a pH of 5 to 9. Alternatively, the parenteral composition may be one designed for slow release in which case the amount of polypeptide per unit dose is in general greater than that required when a conventional injectable formulation is used. A preferred slow release formulation is, for example, a continuous release formulation, for example a formulation of the type described in European Patent Specification No. 58481. A preferred slow release parenteral formulation contains from 10 to 100 mg of polypeptide per unit dose.

The composition of the invention will normally be administered such that a daily oral dose will be from 0.1 mg/kg, to 50 mg/kg and a daily parenteral dose, will be from 20 micrograms/kg to 10 mg/kg.

According to a further feature of the invention there is provided a method for producing a bombesin-antagonist effect in a warm-blooded animal, such as man, in need of such treatment which comprises administering to said animal an effective amount of a polypeptide of formula I or a pharmaceutically-acceptable salt thereof. The invention also provides the use of such a polypeptide of formula I or a pharmaceutically-acceptable salt thereof in the production of a new medicament for use in the treatment of a disease or medical condition mediated by bombesin or a bombesin-like peptide.

A polypeptide of the invention may be used in the treatment of, for example, malignant disease, for example malignant disease in the lung, such as human small cell lung cancer, for example, malignant disease in the pituitary gland, adrenal gland or within the skin. A polypeptide of the invention may also be used in the treatment of conditions associated with the over-production of bombesin or bombesin-like peptides, for example the over-production of gastrin in the gut. The production of gastrin in animals has been linked to the suppression of the release of growth hormone and prolactin. A polypeptide of the invention may therefore be used to promote the availability of growth hormone in man or animals in need of such treatment. A polypeptide of the invention may also be used in the treatment of conditions associated with the failure of normal physiological control of the regulation of gastric acid secretion.

The invention is illustrated, but not limited, by the following Examples in which, unless otherwise stated:

(i) The structures of all polypeptide compounds of the invention were confirmed by mass spectroscopy. Fast-atom bombardment (FAB) mass spectral data were obtained using a VG Analytical MS9 spectrometer and xenon gas. Positive ion data were collected.

(ii) The structures of all polypeptide compounds of the invention were also confirmed by acid hydrolysis and analysis of the resultant amino acids. The hydrolysates were produced by heating each polypeptide or protected polypeptide with 6N-hydrochloric acid containing 1% w/v phenol in a sealed evacuated tube at 110° C. for between 16 and 48 hours. The amino acid composition of each hydrolysate was determined with a LKB Model No. 4151 Amino Acid Analyser, and in each case the result was in agreement with the expected composition.

(iii) Crude polypeptide compounds were generally purified by chromatography of a solution of the polypeptide in a 30:70:0.1 v/v mixture of acetonitrile, water and TFA on a preparative reverse-phase column of silica gel (20 mm by 25 cm) using, as eluent at a flow rate of 12–80 ml per minute, a solvent gradient ranging from a 30:70:0.1 v/v to a 70:30:0.1 v/v mixture of acetonitrile, water and TFA. The eluate was monitored continuously by UV absorbance at a value between 230 and 280 nm and the portion of eluate corresponding to the major peak of UV absorbance was collected, evaporated by rotary evaporation in vacuo and the residue was freeze-dried.

(iv) The following abbreviations are used:

| | |
|---|---|
| DMF = | N,N-dimethylformamide, |
| TFA = | trifluoroacetic acid, |
| DCCI = | N,N'-dicyclohexylcarbodiimide, |
| DICI = | N,N'-diisopropylcarbodiimide, |
| (Boc)$_2$O = | di-tert-butyl dicarbonate, |
| Boc = | tert-butoxycarbonyl |
| Tos = | tosyl (p-tolylsulphonyl) |
| Z = | benzyloxycarbonyl |
| Ac = | acetyl |
| OBut = | tert-butoxy |

EXAMPLE 1

Solid phase synthesis, using a Biosearch (SAM 2) peptide synthesiser, of 4-Pyridyl—CO—His—Trp—Ala—Vla—N—Ala—His—Leu—OMe A hydroxymethylated polystyrene-divinylbenzene resin was used. Boc—Leo—O—[resin] 1.0 g, 0.4 mmol) was placed in the reaction vessel and the following sequence of operations was used to couple Boc—His(-Tos):

| Step | Reagents and Operations | Reaction Time (min) |
|---|---|---|
| 1 | wash with CH$_2$Cl$_2$ (3 times) | |
| 2 | add a 45:52.5:2.5 v/v mixture of TFA, CH$_2$Cl$_2$ and anisole | 1 |
| 3 | add a 45:52.5:2.5 v/v mixture of TFA, CH$_2$Cl$_2$ and anisole | 20 |
| 4 | wash with CH$_2$Cl$_2$ | |
| 5 | wash with DMF (2 times) | |
| 6 | wash with CH$_2$Cl$_2$ | |
| 7 | add a 1:9 v/v mixture of diisopropylethylamine and CH$_2$Cl$_2$ (3 times) | 0.7 |
| 8 | wash with CH$_2$Cl$_2$ (4 times) | |
| 9 | wash with DMF | |
| 10 | wash with CH$_2$Cl$_2$ | |
| 11 | add Boc—His(Tos) (3.3 mmol) and DICI (3.3 mmol) in DMF | 110 |
| 12 | wash with DMF (2 times) | |
| 13 | wash with CH$_2$Cl$_2$ | |
| 14 | add a 1:9 v/v mixture of diisopropylethylamine and CH$_2$Cl$_2$ | 0.7 |
| 15 | wash with DMF | |
| 16 | add acetic anhydride | 30 |
| 17 | wash with DMF (2 times) | |

The cycle of steps 1 to 17 was repeated except that in step 11, in place of Boc—His(Tos), each of the following reagents was introduced in turn, once per cycle:

Boc—D—Ala, Boc—Ala, Boc—Trp and Boc—His(-Tos).

The Boc group at the N-terminus was removed using steps 1 to 10 described above.

A mixture of the polypeptide so formed, still attached to the resin, isonicotinic acid (0.5 g, 4 mmol), N,N'-diisopropylcarbodiimide (0.5 g, 4 mmol) and DMF (20 ml) was stirred at ambient temperature for 1 hour. The resin was filtered off and washed with DMF.

The polypeptide so formed, still attached to the resin, was treated with a 1M 1-hydroxybenzotriazole solution in DMF (20 ml) for 1 hour. The resin was washed with DMF (3 times) and CH$_2$C$_{12}$ (3 times). There was thus obtained 4-pyridyl—CO—His—Trp—Ala—Val—D—Ala—His—Leu—O—[resin].

The polypeptide was cleaved from the resin and purified using the following procedure:

A mixture of the polypeptide so formed, still attached to the resin, methanol (50 ml), DMF (50 ml) and triethylamine (3-ml) was stirred at ambient temperature for 3 days. The mixture was filtered and the resin was washed with DMF (4×20 ml) and methanol (4×20 ml). The resin was retreated with methanol and triethylamine for 3 days. The filtrates and washings were combined and evaporated by rotary evaporation in vacuo to give an oil which was purified by chromatography and freeze-dried. There was thus obtained as a white powder (0.042 g) 4-Pyridyl—CO—His—Trp—Ala—Val—D—Ala—His—Leu—OMe. Mass Spectrum: m/e 952.

All of the Boc protected amino-acids were commercially available.

EXAMPLE 2

A mixture of the polypeptide of the invention described in Example 1 (12 mg) and a 33% w/v solution of methylamine in ethanol (2-ml) was stirred at ambient temperature for 8 hours. The mixture was evaporated by rotary evaporation in vacuo and the residual oil was freeze-dried. There was thus obtained, as a white powder (11 mg), 4-Pyridyl—CO—His—Trp—Ala—Val—D—Ala—His—Leu—NHMe. Mass Spectrum: m/e 951.7 (P+1).

EXAMPLE 3

The process described in Example 1 was repeated using the appropriate C-terminus protected amino acid attached by an ester link to the resin and the appropriate protected amino acid. Those polypeptides, still attached to the resin, which contained a His(Tos) protected amino acid were treated with 1-hydroxybenzotriazole as described in Example 1. There were thus obtained the polypeptides described in the following table, the structures of which were confirmed by mass spectroscopy and by analysis of their amino acid content after acidic hydrolysis.

TABLE I

| Ex. 3 No. | Polypeptide | Mass m/e (P + 1) |
| --- | --- | --- |
| 1 | 4-Pyridyl-CO—Trp—Ala—Val—D-Ala—His—Leu—OMe | 815 |
| $2^{a,b}$ | 4-Pyridyl-CO—His—Trp—Ala—Val—D-Ala—His—MeLeu—OMe | 966 |
| $3^a$ | 3-Pyridyl-CO—His—Trp—Ala—Val—D-Ala—His—MeLeu—OMe | 966 |
| $4^a$ | 2-Indolyl-CO—His—Trp—Ala—Val—D-Ala—His—MeLeu—OMe | 1004 |

Notes (a) Boc—MeLeu—O—[resin] was obtained as follows: A mixture of a hydroxymethylated polystyrene-divinylbenzene resin (10 g, 4 mmol), Boc—MeLeu (1 g, 4 mmol), DCCI (0.83 g, 4 mmol), dimethylaminopyridine (50mg, 0.4 mmol) and methylene chloride (100 ml) was stirred at ambient temperature for 2 days. Second portions of Boc—MeLeu (2-g), DCCI (1.7 g) and dimethylaminopyridine (200 mg) were added and the mixture was stirred at ambient temperature for a further 2 days. The resin was filtered off, washed in succession with methylene chloride, DMF and isopropanol and then dried.

A mixture of the Boc—MeLeu—O—[resin] so obtained, acetic anhydride (1.12 ml), triethylamine (1.68 ml) and DMF (50 ml) was stirred at ambient temperature for 1 hour to ensure acetylation of any remaining hydroxymethyl groups on the resin. The resin was filtered off, washed as above and dried.

(b) The coupling of isonicotinic acid was performed at a reaction temperature of 45° C. for 1 hour.

EXAMPLE 4

Solid phase synthesis, using an Applied Biosystems 430A Peptide synthesiser, of
4-Pyridyl—CO—Trp—Ala—Val—D—Ala—His—MeLeu—OMe.

A hydroxymethylated polystyrene-divinylbenzene resin was used. Boc—MeLeu—O—[resin] (1 g, 0.4 mmol) was placed in the reaction vessel and the following sequence of steps was used to couple Boc—His(-Tos):

| Step | Reagents and Operations | Reaction Time (min) |
| --- | --- | --- |
| 1 | wash with $CH_2Cl_2$ (3 times) | |
| 2 | 2:1 v/v mixture of TFA and $CH_2Cl_2$ | 1.3 |

-continued

| Step | Reagents and Operations | Reaction Time (min) |
| --- | --- | --- |
| 3 | 1:1 v/v mixture of TFA and $CH_2Cl_2$ | 18 |
| 4 | wash with $CH_2Cl_2$ (3 times) | |
| 5 | 1:9 v/v mixture of diisopropylethylamine and DMF (2 times) | 1 |
| 6 | wash with DMF (5 times) | |
| 7 | Boc—His(Tos) anhydride (0.8 mmol) in DMF | 26 |
| 8 | wash with $CH_2Cl_2$ (5 times) | |

The cycle of steps 1 to 8 was repeated except that in step 7, in place of Boc—His(Tos) anhydride, each of the following reagents was introduced in turn, once per cycle (the reaction times are indicated in parenthesis) Boc—D—Ala anhydride (16 min), Boc—Val anhydride (26 min), Boc—Ala anhydride (16 min) and Boc—Trp anhydride (26 min).

There was thus obtained Boc—Trp—Ala—Val—D—Ala—His(Tos) MeLeu—O—resin]. The Boc group at the N-terminus was removed using steps 1 to 6 described above. A mixture of the polypeptide so formed, isonicotinic acid (0.5 g, 4 mmol), DICI (0.5 g, 4 mmol) and DMF (20 ml) was stirred at ambient temperature for 1 hour. The resin was filtered off and washed with DMF. The polypeptide so formed was treated with a 1M 1-hydroxybenzatriazole solution in DMF (20 ml) for 1 hour. The resin was washed with DMF (3 times) and $CH_2Cl_2$ (3 times). There was thus obtained:
4-Pyridyl—CO—Trp—Ala—Val—D—Ala—His—MeLeu—O—[resin].

The polypeptide was cleaved from the resin and purified using the following procedures:

A mixture of the polypeptide-resin, methanol (20 ml), DMF (20 ml) and diisopropylethylamine (3-ml) was stirred at ambient temperature for 3 days. The mixture was filtered and the resin was washed with DMF (4×20 ml) and methanol (4×20 ml). The filtrate and washings were combined and evaporated by rotary evaporation in vacuo to give an oil which was freeze-dried. The crude product so obtained was purified by chromatography and freeze-dried. There was thus obtained as a white powder (0.062 g), 4-Pyridyl—CO—Trp—Ala—Val—N—Ala—His—MeLeu—OMe; Mass Spectrum: m/e 829 (P+1).

The Boc protected amino acid anhydrides were prepared in an activator vessel by the reaction of a solution of the appropriate Boc protected amino acid (1.6 mmol) in $CH_2Cl_2$ with DCCI (0.8 mmol) at ambient temperature. The mixture was filtered and transferred to a concentrator vessel, the solvent was evaporated, DMF was added and the solution of Boc protected amino acid anhydride was transferred to the reaction vessel at step 7 outlined above.

The Boc protected amino acids, were obtained commercially from Applied Biosystems Ltd. Boc—His(-Tos) as its dicyclohexylamine salt was obtained commercially from Applied Biosystems Ltd, the free base being obtained by passing a solution of the salt in $CH_2Cl_2$ through a Biorad AG50-X8 ion exchange column.

EXAMPLE 5

The process described in Example 4-was repeated using the appropriate C-terminus protected amino acid attached by an ester link to the resin; the appropriate protected amino acid anhydrides or where indicated the appropriate protected amino acid 1-hydroxybenzotriazole ester and, where necessary, the appropriate carboxylic acid in place of isonicotinic acid.

There were thus obtained the polypeptides described in the following table, the structures of which were confirmed by mass spectroscopy and by analysis of their amino acid content after acidic hydrolysis.

TABLE II

| Ex. 5 No. | Polypeptide | Mass m/e (P + 1) |
|---|---|---|
| 1a | 4-Pyridyl-CO—His—Trp—Ala—Val—D-Ala—Lys(Z)—Leu—OMe | 1077 |
| 2b | 4-Pyridyl-CO—His—Trp—Ala—Val—D-Ala—Lys(Z)—MeLeu—OMe | 1091 |
| 3 | 2-Pyrazinyl-CO—His—Trp—Ala—Val—D-Ala—His—Leu—OMe | 953 |
| 4b,c | 4-Pyridyl-CO—Lys(CO—4-Pyridyl)-Trp—Ala—Val—D-Ala—His—Leu—OMe | 1062 |
| 5 | 3-Indolyl-CO—His—Trp—Ala—Val—D-Ala—His—Leu—OMe | 990 |

Notes (a) The isonicotinic was coupled using a mixture of DCCI and 1-hydroxybenzotriazole in place of DICI. The mixture was stirred at ambient temperature for 16 hours.

(b) The isonicotinic acid was coupled using a mixture of DICI and N-hydroxysuccinimide. The mixture was stirred at ambient temperature for one hour.

(c) Boc—Lys(Z) anhydride was used but during the coupling of the isonicotinic acid there was exchange of the Z group and an isonicotinoyl group on the side-chain amino group.

EXAMPLE 6

The process described in Example 2 was repeated using the appropriate polypeptide of the invention having a methyl ester at the C-terminus. There were thus obtained the polypeptides described in the following table, the structures of which were confirmed by mass spectroscopy and by analysis of their amino acid content after acidic hydrolysis.

TABLE III

| Ex. 6 No. | Polypeptide | Mass m/e (P + 1) |
|---|---|---|
| 1 | 4-Pyridyl-CO—His—Trp—Ala—Val—D-Ala—His—MeLeu—NHMe | 965.9 |
| 2 | 4-Pyridyl-CO—His—Trp—Ala—Val—D-Ala—Lys(Z)—Leu—NHMe | 1075 |
| 3a | 4-Pyridyl-CO—His—Trp—Ala—Val—D-Ala—Lys(COCH3)—Leu—NHMe | 985 |
| 4a | 4-Pyridyl-CO—His—Trp—Ala—Val—D-Ala—Lys(COPh)—Leu—NHMe | 1047 |
| 5a | 4-Pyridyl-CO—His—Trp—Ala—Val—D-Ala—Lys(COCH2Ph)—Leu—NHMe | 1061.5 |
| 6a | 4-Pyridyl-CO—His—Trp—Ala—Val—D-Ala—Lys(COCH2CH2Ph)—NHMe | 1075.3 |

Notes (a) A mixture of the polypeptide described as Compound No. 2 in Example 6 (0.124 g), palladium-on-charcoal catalyst (10%, 50 mg) and glacial acetic acid (6 ml) was stirred at ambient temperature under an atmosphere of hydrogen for 4-hours. The mixture was filtered and the catalyst was washed with water. The combined filtrates were freeze-dried to give the polypeptide product (0.125 g) 4-Pyridyl—CO——His—Trp—Ala—Val—D—Ala—Lys—Leu—NHMe The polypeptide so obtained was acylated by reaction with the 1-hydroxybenzotriazole ester of the appropriate carboxylic acid selected from acetic acid, benzoic acid, phenylacetic acid and 3-phenylpropionic acid. The acylation was carried out by mixing the polypeptide, the appropriate ester, dimethylaminopyridine, 1-hydroxybenzotriazole and DMF and stirring the mixture at ambient temperature for 16 hours. The solvent was evaporated by rotary evaporation in vacuo and the residue was purified by chromatography and freeze-dried.

What is claimed includes the following:

1. A polypeptide of formula I:

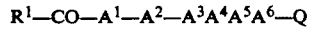

$$R^1—CO—A^1—A^2—A^3A^4A^5A^6—Q \qquad I$$

wherein $R^1$ is a 5- or 6-membered unsaturated heterocyclic ring which contains one, two or three nitrogen atoms, which heterocyclic ring may be a single ring or may be fused to a benzo-ring, and which heterocyclic ring may optionally bear one or two substituents selected from halogeno, (1–4C)alkyl, (1–4C)alkoxy, hydroxy, cyano and nitro;

wherein $A^1$ is a direct link to $A^2$, or is His, D—His, MeHis, EtHis, PrHis, D—Gln, D—Glu(OMe), Leu, MeLeu, D—Leu, Lys(CO 4-Pyridyl), Pal, D—Pal, Phe, D—Phe, Pro, Arg, Glu, His($\tau$-Me), His($\pi$-Me), His(COPh) or Trp;

wherein $A^2$ is Trp, MeTrp, Trp(Me), Trp(For), Val, DL—Flg, L—Nal, pcF, Leu, Lys, Pal or Cha;

wherein $A^3$ is Ala, MeAla, Aib, Gly, Pro, Leu, Phe, Ser, Val, L—Nal, Thr or Glu; wherein $A^4$ is Val, Aib, Leu, Ile, Thr, Phe, Ser or DL—Flg;

wherein $A^5$ is Gly, Sar, D—Ala, D—Ser, D—Ser(CH2Ph), D—pcF, D—Ala(NH2), D—Ala(NHZ(Cl)), Aib, D—Pro, D—Lys, D—Arg, Ac3c, Ac5c or Ac6c;

wherein $A^6$ is His, MeHis, His($\tau$-Me), His($\pi$-Me), Aib, Val, Leu, Ala, Ile, Ahx, Ape, Met, Pro, Phe, Gln, Lys, Lys(Z), Lys(COCH3), Lys(COPh), Lys(COCH2Ph), Lys(COCH2CH2Ph), Pal, Ser, Ser(CH2Ph), Thr, Thr(CH2Ph), Glu, Asp, Asp(OBut), Trp or L—Nal; and wherein Q is a group of the formula —$A^7.R^2$ in which $A^7$ is Leu, D—Leu, MeLeu, Ile, MeIle, Ahx, MeAhx, Aib, Pro, Val, MeVal, Phe, Ape, MeApe, Met, Ser, Gln or Trp and $R^2$ is hydroxy or amino; or $R^2$ is (1–3C)alkylamino, dialkylamino of up to 4 carbon atoms, or (1–3C)alkoxy, each optionally bearing a hydroxy, (1–3C)alkoxy, amino, (1–6C)alkylamino, dialkylamino of up to 8 carbon atoms, or phenyl (1–3C)alkylamino substituent, other than in a position alpha to an oxygen or nitrogen atom, or a fluoro-(1–3C)alkyl or phenyl substituent; or $R^2$ is (3–6C)cycloalkylamino, N-alkyl-N-cycloalkylamino of up to 8 carbon atoms, or dicycloalkylamino of up to 12 carbon atoms; or $R^2$ is 1-pyrrolidinyl, piperidino, morpholino, 1-piperazinyl or 4-methylpiperazin-1-yl; or Q is (1–6C)alkoxy, (1–10C)alkylamino or dialkylamino of up to 10 carbon atoms each optionally bearing a hydroxy, amino, (1–3C)alkoxy, (1–6C)alkylamino, dialkylamino of up to 8 carbon atoms, phenyl-(1–3C)alkylamino substituent, other than in a position alpha to an oxygen or nitrogen atom, or a phenyl substituent; or Q is phenyl-(1-3C)alkylamino; or Q is (3-6C)cycloalkylamino, N-alkyl-N-cycloalkylamino of up to 8 carbon atoms or dicycloalkylamino of up to 12 carbon atoms; or Q is 1-azetidinyl, 1-pyrrolidinyl, piperidino, morpholino, 1-piperazinyl or 1-homopiperidinyl each optionally bearing on any available position, including on any available nitrogen atom, a substituent selected from (1-6C)alkyl, phenyl and phenyl-(1-3C)alkyl; and wherein within $R^2$ or Q a phenyl group may optionally bear a substituent selected from halogeno, (1-4C)alkyl, (1-4C)alkoxy, hydroxy and cyano;

or a pharmaceutically-acceptable salt of said polypeptide.

2. A polypeptide compound of the formula I as claimed in claim 1 wherein $R^1$ is pyrrolyl, indolyl, pyridyl, quinolyl, imidazolyl, pyrazolyl, pyrimidinyl, pyrazinyl or 1,2,4-triazolyl which may optionally bear one or two substituents selected from fluoro, chloro, methyl, methoxy, hydroxy and cyano;

wherein $A^1$ is a direct link to $A^2$, or is His, D—His, MeHis, EtHis, PrHis, D—Gln, Glu(OMe), Leu, MeLeu, Lys(CO-4-Pyridyl), Pal, D—Pal, Phe, Pro, His($\tau$-Me), His($\pi$-Me) or Trp;

wherein $A^2$ is Trp, MeTrp, Trp(Me), Trp(For), L—Nal, pcF or Pal;

wherein $A^3$ is Ala, MeAla, Gly, Leu, Ser, Val or Thr;

wherein $A^4$ is Val, Aib, Leu, Ile or Thr;

wherein $A^5$ is Gly, Sar, D—Ala, D—Ser, D—Ser(CH$_2$Ph), D—pcF, Aib, D—Pro or D—Lys:

wherein $A^6$ is His, MeHis, His($\tau$-Me), His($\pi$-Me), Val, Leu, Pro, Phe, Gln, Lys(Z), Lys(COCH$_3$), Lys(COPh), Lys(COCH$_2$Ph), Lys(COCH$_2$CH$_2$Ph), Pal, Ser. Ser(CH$_2$Ph), Thr, Thr(CH$_2$Ph), Trp or L—Nal; and wherein Q is a group of the formula —$A^7.R^2$ in which $A^7$ is Leu, D—Leu, MeLeu, Ile, MeIle, Ahx, Aib, Val, MeVal, Phe, Ape or Met and $R^2$ is hydroxy or amino; or $R^2$ is (1-3C)alkylamino (especially methylamino and ethylanino), dialkylamino of up to 4 carbon atoms (especially dimethylamino and N-ethyl-N-methylamino) or (1-3C)alkoxy (especially methoxy and ethoxy), each optionally bearing an amino, (1-6C)alkylamino especially methylamino, ethylamino, isobutylamino and isopentylamino) or phenyl-(1-3C)alkylamino (especially benzylamino and phenethylamino) substituent, other than in a position alpha to an oxygen or nitrogen atom, or a fluoro-(1-3C)alkyl (especially trifluoromethyl) or phenyl substituent; or $R^2$ is (3-6C)cycloalkylamino (especially cyclopentylamino and cyclohexylamino); or $R^2$ is 1 -pyrrolidinyl, piperidino, morpholino or 1-piperazinyl; or Q is (1-6C)alkoxy (especially methoxy, isopropoxy, isobutoxy, tert-butoxy and isopentyloxy), (1-10C)alkylamino (especially methylamino, isobutylamino, isopentylamino, 1-ethylpropylamino, 1-ethylpentylamino, 1,3-dimethylbutyamino and 1,4-dimethylpentylamino) or dialkylamino of up to 10 carbon atoms (especially dimethylamino, N-ethyl-N-methylamino and N-isopentyl-N-methylamino), each optionally bearing an amino, (1-6C)alkylamino (especially methylamino, isopropylamino, isobutylamino and isopentylamino) or phenyl-(1-3C)alkylamino (especially benzylamino and phenethylamino) substituent, other than in a position alpha to an oxygen or nitrogen atom, or a phenyl substituent; or Q is phenyl-(3-6C)alkylamino (especially benzylamino and phenethylamino); or Q is (3-6C)alkylamino (especially cyclopentylamino and cyclohexylamino); or Q is 1-pyrrolidinyl, piperidino, morpholino or 1-piperazinyl, each optionally bearing on any available position, including on any available nitrogen atom, a substituent selected from (1-6C)alkyl (especially methyl and ethyl), phenyl and phenyl-(1-3C)alkyl (especially benzyl and phenethyl); and wherein within Q a phenyl group may optionally bear a substituent selected from chloro, methyl, methoxy and hydroxy; and the pharmaceutically-acceptable salts thereof.

3. A polypeptide compound of the formula I as claimed in claim 1 wherein $R^1$ is 2-pyrrolyl, 2-indoly, 3-indolyl, 2-pyridyl, 3-pyridyl, 4-pyridyl, 2-imidazolyl, 4-pyrazolyl, 2-pyrimidinyl, 4-pyrimidinyl, 5-pyrimidinyl or 2-pyrazinyl which may optionally bear a substituent selected from chloro, methyl, methoxy, hydroxy or cyano;

$A^1$ is His, D—His, D—Gln, D—Glu(OMe), Leu, Pal, D—Pal, Phe, Pro, His($\tau$-Me) or His($\pi$—Me);

$A^2$ is Trp or MeTrp; $A^3$ is Ala, MeAla or Aib; $A^4$ is Val;

$A^5$ is Gly, Sar, D—Ala, D—Ser. D—Ser(CH$_2$Ph), D—pcF, Aib or D—Pro;

$A^6$ is His, MeHis, His($\tau$-Me), His($\pi$-Me), Leu, Pro, Phe, Gln, Lys, Lys(Z) or Pal; and Q is a group of the formula —$A^7.R^2$ in which $A^7$ is Leu, MeLeu, Ile, Ahx, Val or Phe and $R^2$ is methoxy, amino or methylamino, each optionally bearing a trifluoromethy or phenyl substituent, or $R^2$ is ethoxy or ethylamino, each optionally bearing an amino, methylamino, ethylamino, isobutylamino, isopentylamino, benzylamino or phenthylamino substituent, other than in a position alpha to an oxygen or nitrogen atom, or a trifluoromethyl or phenyl substituent;

or $R^2$ is cyclopentylamino or 1-pyrrolidinyl;

or q is methoxy, isopropoxy, isobutoxy, isopentyloxy, methylamino, isobutylamino, isopentylamino, 1-ethylpropylamino or 1,3-dimethylbutylamino, each optionally bearing an amino, methylamino, isopropylamino, isobutylamino, isopentylamino, benzylamino or phenethylamino substituent, other than in a position alpha to an oxygen or nitrogen atom, or a phenyl substituent, or Q is benzylamino or phenethylamino;

or Q is cyclopentylamino, cyclohexnylamino, piperidino, 4-phenylpiperidino, morpholino or 4-benzylpiperazin-1-yl;

and the pharmaceutically-acceptable acid-addition salts thereof.

4. A polypeptide compound of the formula I as claimed in claim 1.

wherein $R^1$ is 2-pyrrolyl, 2-indoll, 3-indolyl, 2-pyridiyl, 3-pyridyl, 4-pyridyl, 2-imidazolyl, 4-pyrazolyl, 2-pyrimidinyl, 4-pyrimidinyl, 5-pyrimidinyl or 2-pyrazinyl which may optionally bear a substituent selected from chloro, methyl, methoxy, hydroxy or cyano;

$A^1$ is a direct link to $A^2$, or is His D—His, D—Gln, D—Glu(OMe), Leu, MeLeu, Lys(Co-4-Pyridyl), Pal, D—Pal, Phe, Pro, His($\tau$-Me) or His($\pi$-Me);

$A^2$ is Trp or MeTrp; $A^3$ is Ala, MeAla or Ser; $A^4$ is Val or Ile;

$A^5$ is Gly, Sar, D—Ala, D—Ser, D—Ser, D—Ser($CH_2$Ph), D—pcF, Aib or D—Pro;

$A^6$ is His, MeHis, His($\tau$-Me), His($\pi$-Me), Val, Leu, Pro, Phe, Gln, Lys(Z), Lys($COCH_3$), Lys(COPh), Lys($COCH_2$Ph), Lys($COCH_2CH_2$Ph), Pal, Ser, Ser($CH_2$Ph), Thr, Thr($CH_2$Ph), Trp or L—Nal; and Q is a group of the formula —$A^7.R^2$ in which $A^7$ is Leu, MeLeu, Ile, Ahx, Val or Phe and $R^2$ is methoxy, amino or methylamino, each optionally bearing a trifluoromethy or phenyl substituent, or $R^2$ is ethoxy or ethylamino, each optionally bearing an amino, methylamino, ethylamino, isobutylamino, isopentylamino, benzylamino or phenethylamino substituent, other than in a position alpha to an oxygen or nitrogen atom, or a trifluoromethyl or phenyl substituent; or $R^2$ is cyclopentylamino or 1-pyrrolidinyl;

or Q is methoxy, isopropoxy, isobutoxy, isopentyloxy, methyamino, isobutylamino, isopentyamino, 1-ethylpropylamino or 1,3-dimethylbutylamino, each optionally bearing an amino, methylamino, isopropylamino, isobutylamino, isopentylamino, beanzylamino or phenethylamino substituent, other than in a position alpha to an oxygen or nitrogen atom, or a phenyl substituent, or Q is benzylamino or phenethylamino;

or Q is cyclopentylamino, cyclohexylamino, piperidino, 4-phenylpiperidino, morpholino or 4-benzylpiperazin-1-yl; and the pharmaceutically-acceptable acid-addition salts thereof.

5. A polypeptide compound of the formula I as claimed in claim 1 wherein $R^1$ is 3-pyridyl, 4-pyridyl, 2-pyrazinyl, 2-indolyl or 3-indolyl;

$A^1$ is His;

$A^2$ is Trp; $A^3$ is Ala; $A^4$ is Val;

$A^5$ is D—Ala; $A^6$ is His, Lys(Z), Lys($COCH_3$(, Lys(-$COCH_2$Ph) or Lys($COCH_2CH_2$Ph); and Q is a group of the formula —$A^7.R^2$ in which $A^7$ is Leu or MeLeu and $R^2$ is methoxy or methylamino;

and the pharmaceutically-acceptable salts thereof.

6. The polypeptide:
4-Pyridyl—CO—His—Trp—Ala—Val—D—Ala—His—Leu—OMe or
4-Pyridyl—CO—His—Trp—Ala—Val—D—Ala—His—Leu—NHMe.

7. The polypeptide:
4-Pyridyl—CO—His—Trp—Ala—Val—D—Ala—His—MeLeu—OMe,
3-Pyridyl—CO—His—Trp—Ala—Val—D—Ala—His—MeLeu—OMe,
4-Pyridyl—CO—His—Trp—Ala—Val—D—Ala—Lys(Z)—MeLeu—OMe,
3-Indolyl—CO—His—Trp—Ala—Val—D—Ala—His—Leu—OMe,
4-Pyridyl—CO—His—Trp—Ala—Val—D—Ala—His—MeLeu—NHMe
4-Pyridyl—CO—His—Trp—Ala—Val—D—Ala—Lys(Z)—Leu—NHMe,
4-Pyridyl—CO—His—Trp—Ala—Val—D—Ala—Lys($COCH_2$Ph)—Leu—NHMe or
4-Pyridyl—CO—His—Trp—Ala—Val—D—Ala—Lys($COCH_2CH_2$Ph)—Leu—NHMe.

8. A pharmaceutical composition suitable for producing a bombesin-antagonist effect in a warm-blooded animal in need of such treatment which comprises an effective amount of polypeptide of formula I as claimed in any one of claims 1 to 5, or a pharmaceutically-acceptable salt thereof, in association with a pharmaceutically-acceptable diluent or carrier.

9. A method for producing a bombesin-antagonist effect in a warm-blooded animal, in need of such treatment which comprises administering to said animal an effective amount of a polypeptide of formula I as claimed in any one of claims 1 to 5, or a pharmaceutically-acceptable salt thereof.

* * * * *